United States Patent [19]

Timár et al.

[11] Patent Number: 4,866,089
[45] Date of Patent: Sep. 12, 1989

[54] CHROMENE DERIVATIVES AND PESTICIDAL COMPOSITION COMPRISING THE SAME

[75] Inventors: Tibor Timár; Kálmán Zsupán; János Répási; Irén Borsos née Safranek, all of Tiszavasvári; István Kiss, Szeged; András Fodor, Szeged; Péter Maróy, Szeged, all of Hungary

[73] Assignee: Alkaloida Vegyeszeti Gyar, Tiszavasvari, Hungary

[21] Appl. No.: 166,806

[22] Filed: Mar. 3, 1988

Related U.S. Application Data

[63] Continuation of Ser. No. 908,946, Sep. 16, 1986, abandoned, which is a continuation of Ser. No. 580,647, Feb. 16, 1984, abandoned.

[30] Foreign Application Priority Data

Feb. 16, 1983 [HU] Hungary ............................ 520/83

[51] Int. Cl.$^4$ .................. A01N 43/16; C07D 311/64
[52] U.S. Cl. ............................... 514/456; 549/408
[58] Field of Search ................... 549/408; 514/456

[56] References Cited

U.S. PATENT DOCUMENTS

| | | | |
|---|---|---|---|
| 2,354,492 | 7/1944 | Adams | 549/408 |
| 4,162,326 | 7/1979 | Mihailovski | 549/408 |
| 4,323,505 | 4/1982 | Hashimoto et al. | 549/408 |
| 4,542,150 | 9/1985 | Bowers | 514/456 |

FOREIGN PATENT DOCUMENTS

| | | | |
|---|---|---|---|
| 0040637 | 3/1980 | Japan | 549/408 |
| 0109779 | 7/1982 | Japan | 549/408 |
| 7513616 | 11/1975 | Netherlands | 549/408 |
| 0213149 | 5/1941 | Switzerland | 549/408 |

OTHER PUBLICATIONS

Chatteyia et al, Indian Journ. Chem. 12 (Dec., 1974), pp. 1256–1258.
Gan et al., C.A., 94, 156,693e (1981-Abstract of Hua Hsueh Hsueh Pao, 38, 451 (1980).

*Primary Examiner*—Nicky Chan
*Attorney, Agent, or Firm*—Herbert Dubno; Jonathan Myers

[57] ABSTRACT

The invention relates to a process for the preparation of chromenes of the general Formula V

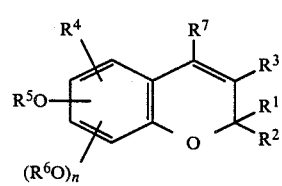

(wherein $R^1$ and $R^2$ are hydrogen, optionally halogeno substituted $C_{1-6}$ alkyl or aryl;
$R^3$ and $R^7$ stand for hydrogen, halogen or $C_{1-6}$ alkyl;
$R^4$ represents $C_{1-8}$ alkyl, aryl, aralkyl or a group containing a carbonyl group;
$R^5$ and $R^6$ stand for $C_{1-10}$ alkyl, aryl, amino, hydroxyalkyl, alkoxyalkenyl, alkylmercaptoalkyl, acyl, carboxy or an ester group or a halogen atom;
n is 0 or 1)
which comprises (a) for the preparation of compounds, in which $R^5$ and $R^6$ stand for different groups, reacting a compound of the general Formula I

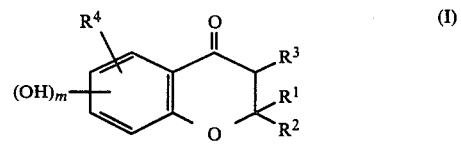

with an approximately equimolar, preferably 0.8–1.5 molar amount of a reactant of the general Formula $R^5$—X—related to the amount of the compound of the general Formula I (wherein $R^5$ has the same meaning as stated above X is halogen) and reacting the O-monosubstituted compound of the general Formula III

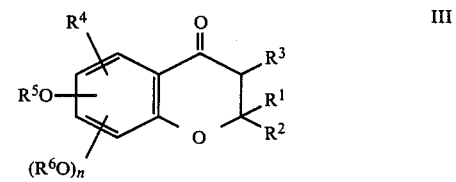

(wherein $R^1$–$R^6$ and n are as stated above) obtained with a 1.1–1.5 molar amount of a compound of the general Formula III (wherein $R^6$ and X are as stated above); or (b) for the preparation of compounds, in which $R^5$ and $R^6$ stand for the same group, reacting a (Abstract continued on next page.)

chromanone of the general Formula I (wherein $R^1$–$R^4$ and m have the meaning as stated above) with a 2–3 molar amount of a compound of the general Formula $R^5$—X-related to the amount of the compound of the general Formula I (wherein $R^5$ and X are as stated above), preferably in the presence of a base, a catalyst and a solvent, and thereafter reducing the O-substituted chromanone derivative of the general Formula III thus obtained (wherein $R^1$–$R^6$ and n are as stated above) and dehydrating the chromanol derivative of the general Formula IV

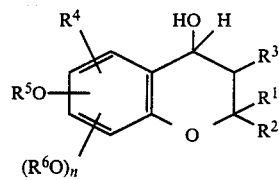

thus obtained (wherein $R^1$–$R^6$ and n are as stated above) in acidic-aqueous medium.

The compounds of the general Formula V are partly new and useful for the preparation of pesticides.

4 Claims, No Drawings

CHROMENE DERIVATIVES AND PESTICIDAL COMPOSITION COMPRISING THE SAME

This is a continuation of co-pending application Ser. No. 908,946, filed on Sept. 16, 1986, which is a continuation of Ser. No. 580,647, filed Feb. 16, 1984, both abandoned.

FIELD OF THE INVENTION

The invention relates to partly new and partly known chromene derivatives, a process for the preparation thereof and pesticidal compositions comprising the same.

The said chromene derivatives are analogues of 7-methoxy-2,2-dimethyl-2H-chromene Precocene-1 (P1) and 6,7-dimethoxy-2,2-dimethyl-2H-chromene Precocene-2 (P2) isolated from nature.

BACKGROUND OF THE INVENTION

The so-called Precocene-1 (P1) and Precocene-2 (P2) are known substances isolated from natural sources. Bowers et al reported about the biological effects of P1 and P2 [W. S. Bowers, T. Ohta et al: Science 193, 542 (1976)]. On the basis of this biological activity it could be expected that P1 and P2 would be useful as a new-type pesticide causing no environmental pollution.

Several articles are published on the biological activity, mechanism of action and metabolism of precocenes. It is known that these compounds exhibit their action by damaging the juvenile hormone producing organ of insects, i.e. by special injury of the so-called "*corpora allata*". On testing the effects of the substances isolated from nature the correlation between the given biological group of effects and the 2H-chromene ring-system was studied. According to experimental results the character and strength of the activity of precocenes depends to a large extent on the pest species, the test method used and from the point of view of chemical structure probably on the number and position of the substituents of the aromatic ring, the strength of the double bond of the pyrane ring and on the electronic and steric parameters of the complete molecule [W. S. Bowers; Martinez-Paro, R.: Science 197 1369 (1977); H. Schooneveld: Experientia 35 363 (1979); W. S. Bowers; Pontif. Acad. Sci. Scr. Varia 41 129 (1976); G. T. Brooks et al: Nature 281 570 (1979); T. Ohta: Kagaku to Seibutsu 17(2) 92 (1979); T. Ohta: Konchu no Seiri to Kagaku 63 (1979); G. Matolcsy et al: Z. Naturforsch. 35b. 1449 (1980); G. T. Brooks et al: Proc. Br. Crop. Prot. Conf. Pests. Dis. 1 273 (1979); G. E. Pratt et al: Nature 284 320 (1980); D. M. Soderlund et al: J. Agr. Food Chem. 28(4) 724 (1980); D. A. Schooley et al: Pestic. Biochem. Physiol. 13(2) 95 (1980); A. P. Ottridge et al: Pestic. Sci. 12(3) 245 (1981)].

As a result of the above research work a number of derivatives being more active than P1 and P2 occuring in nature were obtained, e.g. 6-methoxy-7-ethoxy-2,2-dimethyl-2H-chromene (Precocene 3, P3, 3623) which is ten times more effective than P2.

In the published articles and patent specifications relatively few analogue compounds - about 80-100 derivatives - are disclosed, although the precise study of correlations between biological activity and chemical structure and the selection of the most active derivatives would require much more compounds. This is probably due to the fact that the known synthesis are very complicated.

According to prior art [CHROMENES CHROMANONES and CHROMONES, Edited by G. P. Ellis: John Wiley and Sons London, pages 43-63, (1977)] several routes are known for the preparation of 2H-chromene derivatives, the said routes being independent from each other. The majority of these methods is used for the preparation of P1 and P2 and analogues thereof [W. S. Bowers, T. Ohta: Chem. Pharm. Bull. 25(9) 2788 (1977); D. J. Gale, J. P. K. Wilshire: J. Text. Inst. 12 525 (1979); W. Biernacki, W. Sobotka: Polish J. Chem. 53 2275 (1979); 54 2239 (1980); G. Cardillio et al: Tetr. Lett. 27 2545 (1979); J. Chem. Soc. Shem. Comm. 836 (1979); F. Camps, et al: Tetr. Lett. 40 3901 (1979); 21 2361 (1980); J. Het. Chem. 17 207 and 1377 (1980); Tsukayama et al: Heterocycles 16(6) 955 (1981); A. Banerji, N. C. Goomer: Ind. J. Chem. 20B 144 (1981)].

The following patent specifications are published in this field German Federal Republic patent No. 2,639,671; U.S. Pat. No. 4,162,326; Japanese patent Nos. 73121/79, 15,411/80, 40,637/80 and 43,039/80.

The common feature of the said patent specifications and other publications is that although different synthesis routes are used the preparation of each analogue compound constitutes a specific problem and requires the use of different starting materials.

Thus according to German Federal Republic patent No. 2,639,671 and Japanese patent Nos. 15,411/80 and 40,637/80 P2 is prepared from 3,4-dimethoxy-phenol and P3 being ten times more active from 3-ethoxy-4-methoxy-phenol and the industrial scale production of the said starting materials in a sufficient amount and suitable purity constitutes a rather complicated problem per se.

DISCLOSURE OF THE INVENTION

The present invention is based on the recognition that a large number of biologically active 2H-chromenes of the Formula V

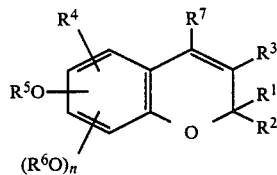

- the majority thereof being new compounds - can be prepared by starting from the suitably substituted hydroxy-4-chromanone derivative of the Formula I.

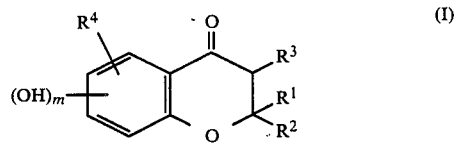

The present invention relates to a new process for the preparation of biologically active chromene derivatives. The intermediates and endproducts prepared by the process of the present invention are partly new compounds.

According to a feature of the present invention there is provided a process for the preparation of chromene derivatives of the Formula V.

According to a further feature of the present invention there are provided new chromanone derivatives of the Formulae VI, VII, VIII, IX, X and XI.

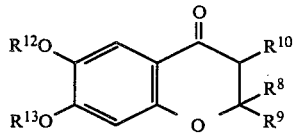

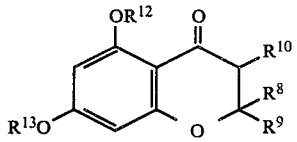

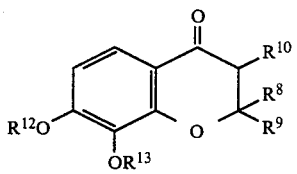

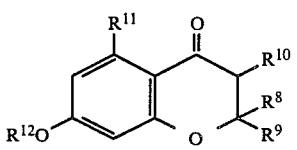

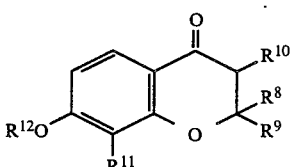

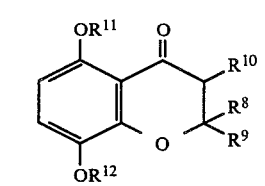

According to a still further feature of the present invention there are provided new chromene derivatives of the Formulae XII, XIII, XIV, XV and XVI.

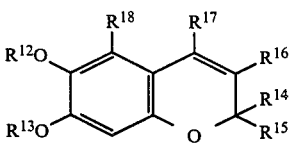  XII

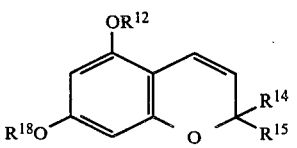  XIII

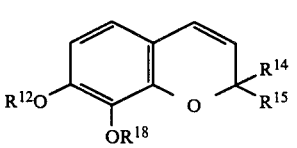  XIV

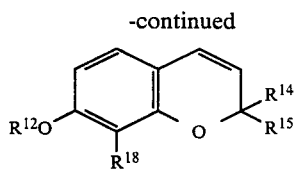  XV

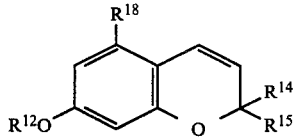  XVI

According to a still further feature of the present invention there are provided pesticidal compositions comprising as active ingredient at least one chromene derivative of the Formula V, particularly a chromene derivative of the Formula XII, XIII, XIV, XV and/or XVI.

In the above Formulae $R^1$ and $R^2$ are hydrogen, optionally halogeno substituted $C_{1-6}$ alkyl or aryl;

$R^3$ and $R^7$ stand for hydrogen, halogen or $C_{1-6}$ alkyl;

$R^4$ represents $C_{1-8}$ alkyl, aryl, aralkyl or a group containing a carbonyl group;

$R^5$ and $R^6$ stand for $C_{1-10}$ alkyl, aryl, amino, hydroxyalkyl, alkoxyalkenyl, alkylmercaptoalkyl, acyl, carboxy or an ester group or a halogen atom;

n is 0 or 1;

m is 1 or 2;

X stands for a halogen atom or a sulfonate, sulfate or epoxy group;

$R^8$ and $R^9$ are hydrogen, methyl, ethyl, trifluormethyl or phenyl;

$R^{10}$ is hydrogen, chlorine, fluorine, bromine or methyl;

$R^{11}$ and $R^{12}$ stand for hydrogen, methyl, acetyl or an aldehyde group;

$R^{14}$, $R^{15}$ and $R^{18}$ are hydrogen or methyl;

$R^{16}$ and $R^{17}$ stand for hydrogen, chlorine or methyl.

The alkyl groups may be straight or branched chained.

According to the present invention there is provided a process for the preparation of chromene derivatives of the Formula V which comprises (a) for the preparation of compounds, in which $R^5$ and $R^6$ stand for different groups, reacting a compound of the Formula I with an approximately equimolar, preferably 0.8–1.5 molar amount of a reactant of the Formula $R^5$—X - related to the amount of the compound of the Formula I (wherein $R^5$ has the same meaning as stated above and X is halogen) and reacting the O-monosubstituted compound of the Formula III

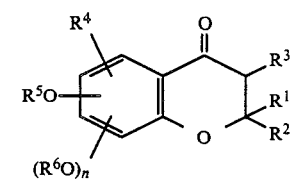  III (wherein $R^1$–$R^6$ and n are as stated above) obtained with a 1.1–1.5 molar amount of a compound of the Formula $R^6$—X related to the amount of the compound of the Formula III (wherein $R^6$ and X are as stated above); or (b) for the preparation of compounds, in which $R^5$ and $R^6$ stand for the same group, reacting a chromanone of the Formula I (wherein $R^1$-$R^4$ and m have the meaning as stated above) with a 2-3 molar amount of a compound of the Formula $R^5$—X - related to the amount of the compound of the Formula I (wherein $R^5$ and X are as stated above), preferably in the presence of a base, a catalyst and a solvent, and thereafter reducing the O-substituted chromanone derivative of the Formula III thus obtained (wherein $R^1$-$R^6$ and n are as stated above) and dehydrating the chromanol derivative of the Formula IV

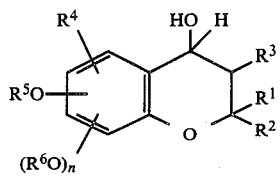

IV thus obtained (wherein $R^1$-$R^6$ and n are as stated above) in acidic-aqueous medium.

The present invention is partly based on the important recognition that the hydroxy groups of the hydroxy-4-chromanone derivatives of the Formula I show different reactivity in O-substitution reactions as a result of their interaction with the carbonyl group in position 4.

This difference can be strengthened by deliberate direction of the reaction conditions to such an extent that selective mono-O-substitution can be carried out with excellent yields. It has been confirmed by various measurements and calculations (PMR, CMR, UV-VIS spectrophotometrical and potentiometric acid-base titrations, pK determinations, "all valence" CNDO quantumchemical calculations, electrostatical potential map calculation) that the hydroxy group in position 7 is the most reactive while the hydroxy groups in positions 5, 6 and 8, respectively, are less reactive. The said difference is illustrated by the determined and calculated pK value summarized in the following Table 1.

TABLE 1

| Substituents | | | $pK_7$ (1.) | $pK_7$ (2.) | $pK_X$ (2.) |
|---|---|---|---|---|---|
| 5-OH | 7-OH | 4-H | 7.4 | 7.0 | 11.6 (X = 5) |
| 6-OH | 7-OH | 4-H | 6.8 | 6.9 | 11.4 (X = 6) |
| 8-OH | 7-OH | 4-H | 7.2 | 7.2 | 11.6 (X = 8) |

Thus when using 6,7-dihydroxy-2,2-dimethyl-4-chromanone the alkylation of the hydroxy group in position 7 can be carried out selectively with a preparative yield of 90-95%. This enables the preparation of the 6-hydroxy-7-alkoxy derivative and thereof by using other alkylating or acylating agents the preparation of "mixed" 6,7-dialkoxy-or 6 acyloxy-7-alkoxy-chromanone derivatives.

INDUSTRIAL APPLICABILITY OF THE INVENTION

The invention enables the preparation of known precocenes and more active analogues thereof from easily available starting materials of the same type by using cheap and known reactants. The present invention provides a simple industrial scale process which enables the use of this compound group in pharmaceutical industry both for synthetic and pharmacological purposes.

MODES OF CARRYING OUT OF THE INVENTION

Further details of the present invention are to be found in the Examples without limiting the scope of protection to the said Examples.

The purity of the compounds disclosed in the Examples is determined by thin layer chromatographical and gas chromatographical methods. The chemical structure of the compounds is confirmed by UV, IR, PMR and CMR spectra and occasionally by elementary analysis.

The PMR spectra are indicated as follows: e.g. 1.45 (3H; 5 t; J=5 Hz), wherein 1.45 = chemical shift 3H = number of protons belonging to the sign t = multiplicity of the sign J = coupling constant designation of multiplets:

s = singulet d = triplet t = triplet q = quartet m = multiplet of higher order sz = broad protracted sign.

PREPARATION OF COMPOUNDS OF THE FORMULA I (1) Preparation of 6,7-dimethoxy-2,2-dimethyl-4-chromanone In 100 ml of acetone 4.2 g (20 millimoles) of 6,7-dihydroxy-2,2-dimethyl-4-chromanone are dissolved and to the solution 8.3 g (60 millimoles) of potassium carbonate and 8.5 g (3.8 ml, 60 millimoles) of methyl iodide are added. The reaction mixture is refluxed for 7 hours whereupon a further amount of 2.8 g (1.2 ml, 20 millimoles) of methyl iodide are added. The reaction mixture is heated to boiling for 3 hours, the suspension formed is cooled under stirring, the precipitated inorganic salt is filtered off, washed twice with 20 ml of acetone each and the acetone is removed. The residue is crystallized from 80% ethanol. Thus 4.5 g of the desired compound are obtained, yield 95.2%. Mp.: 105°-106° C.

PMR (CDCl$_3$): 1.38 (6H; s); 2.64 (2H, s); 3.78 (3H, s); 3.86 (3H, s); 6.5 (1H, s); 7.18 (1H, s).

EXAMPLE 2

Preparation of 6,7-dimethoxy-2,3-dimethyl-4-chromanone

In 80 ml of methyl-ethyl-ketone 4.2 g (20 millimoles) of 6,7-dihydroxy-2,3-dimethyl-4-chromanone are dissolved. To the solution 6.4 g (60 millimoles) of sodium carbonate and 8.5 g (3.8 ml, 60 millimoles) of methyl iodide are added and the reaction mixture is refluxed for 4 hours. After addition of a further 2.8 g (1.2 ml, 20 millimoles) of methyl iodide the reaction mixture is refluxed for further 3 hours. The reaction mixture is worked up according to Example 1. Thus 4.3 g of the desired compound are obtained, yield 91.0%. Mp.: 171°-172° C.

PMR (CDCl$_3$): 1.15 (3H, d, J=5 Hz); 1.45 (3H, d, J=5 Hz); 2.5 (1H, m); 3.8 (3H, s); 3.84 (3H, s); 4.1 (1H, m); 6.32 (1H, s); 7.16 (1H, s)

EXAMPLE 3

Preparation of
5,7-dimethoxy-2,2-dimethyl-4-chromanone

In a mixture of 40 ml of acetone and 40 ml of methyl ethyl ketone 4.2 g (20 millimoles) of 5,7-dihydroxy-2,2-dimethyl-4-chromanone are dissolved, whereupon to the solution 8.3 g (60 millimoles) of potassium carbonate and 5.3 g (3.9 ml, 42 millimoles) of dimethyl sulfate are added under stirring. The reaction mixture is refluxed for 8 hours, the suspension is cooled under stirring, the precipitated inorganic salt is filtered off, washed twice with 20 ml of acetone each and the solvent is removed in vacuo. The residue is taken up in 100 ml of chloroform, washed subsequently with 50 ml of 2% sodium hydroxide solution and 50 ml of water, dried over sodium sulfate and the chloroform is removed in vacuo. The residue is crystallized from 70% ethanol. Thus 4.4 g of the desired compound are obtained, yield 93.1%. Mp.: 104°–105° C.

PMR (CDCl$_3$): 1.4 (6H, s); 2.56 (2H, s); 3.72 (3H, s); 3.8 (3H, s); 5.92 (2H, m)

EXAMPLE 4

Preparation of
7,8-dimethoxy-2,2-dimethyl-4-chromanone

In 50 ml of N,N-dimethyl-formamide 4.2 g (20 millimoles) of 7,8-dihydroxy-2,2-dimethyl-4-chromanone are dissolved and to the solution 6.4 g (60 millimoles) of sodium carbonate and 5.3 g (3.9 ml 42 millimoles) of dimethyl sulfate are added under stirring. The reaction mixture is stirred at 120° C. for 5 hours, poured onto 150 g of crushed ice and extracted three times with 50 ml of chloroform each. The organic phase is washed three times with 100 ml of water each, dried over sodium sulfate and the solvent is distilled off. The residue is crystallized from 75% methanol. Thus 4.0 g of the desired compound are obtained, yield 84.6%. Mp.: 75°–76° C.

PMR (CDCl$_3$): 1.42 (6H, s); 2.64 (2H, s); 3.8 (3H, s); 3.88 (3H, s); 6.56 (1H, d, J=8 Hz); 7.6 (1H, d, J=8 Hz)

EXAMPLE 5

Preparation of 7-methoxy-2,2-dimethyl-4-chromanone

In 40 ml of 5% sodium hydroxide solution 3.84 g (20 millimoles) of 7-hydroxy-2,2-dimethyl-4-chromanone are dissolved whereupon 80 ml of dichloro methane and 0.5 g of triethyl benzyl ammonium chloride are added and the mixture is intensively stirred at room temperature for 20 minutes. After addition of 4.25 g (1.9 ml, 30 millimole) of methyl iodide the reaction mixture is stirred for 2 hours. The organic layer is separated, washed twice with 50 ml of water each, dried over sodium sulfate and evaporated. The residue is crystallized from 80% methanol. Thus 3.9 g of the desired compound are obtained, yield 94.6%. Mp.: 77°–78° C.

PMR (CDCl$_3$): 1.38 (6H, s); 2.6 (2H, s); 3.74 (3H, s); 6.3 (1H, d, J=2 Hz); 6.44 (1H, dd, J=8 Hz, respectively J=2 Hz); 7.7 (1H, d, J=8 Hz)

EXAMPLE 6

Preparation of
7-methoxy-2,2,5-trimethyl-4-chromanone

In 50 ml of acetonitrile 4.9 g (20 millimoles) of the potassium salt of 7-hydroxy-2,2,5-trimethyl-4-chromanone are dissolved and the solution is stirred in the presence of 0.5 g (2 millimoles) of 18-Crown-6 at room temperature for 30 minutes. To the mixture 4.25 g (1.9 ml, 30 millimoles) of methyl iodide are added and the reaction mixture is stirred for a further hour. The inorganic salt is filtered off and the solvent is removed. The residue is taken up in chloroform, washed twice with 50 ml of water each, dried over sodium sulfate and evaporated. The product is crystallized from 90% ethanol. Thus 3.75 g of the desired compound are obtained, yield 85%. Mp.: 86°–88° C.

PMR (CDCl$_3$): 1.36 (6H, s); 2.52 (3H, s); 2.56 (2H, s); 3.7 (3H, s); 6.2 (2H, m).

EXAMPLE 7

Preparation of
7-methoxy-2,2,8-trimethyl-4-chromanone

The reaction is carried out under nitrogen. In 50 ml of a 10% sodium hydroxide solution 4.9 g (20 millimoles) of 7-hydroxy-2,2,8-trimethyl-4-chromanone are dissolved, 2.6 g (2 ml, 21 millimoles) of dimethyl sulfate are added and the reaction mixture is vigorously stirred for 2 hours. The reaction mixture is diluted with 100 ml of icecold water and extracted three times with 50 ml of carbon tetrachloride each. The organic phase is washed twice with 50 ml of water each, dried over sodium sulfate, the solvent is removed and the residue crystallized from 90% methanol. Thus 3.4 g of the desired compound are obtained, yield 78%. Mp.: 105°–107° C.

PMR (CDCl$_3$): 1.45 (6H; s); 2.07 (3H; s); 2.67 (2H; s); 3.90 (3H; s); 6.57 (1H; d; J=10 Hz); 7.77 (1H; J=10 Hz).

EXAMPLE 8

Preparation of
6,7-methylenedioxy-2,2-dimethyl-4-chromanone

A mixture of 20 ml of water, 5.2 g (30 millimole) of dibromo-methane and 0.5 g (1 millimole) of Adogen 464 (Aldrich) is heated to boiling under vigorous stirring. A solution of 4.2 g (20 millimoles) of 6,7-dihydroxy-2,2-dimethyl-4-chromanone and 50 ml of a 5% sodium hydroxide solution is added dropwise within 2 hours and heated to boiling for a further hour. The mixture is diluted with 100 ml of water and extracted twice with 50 ml of chloroform each. The organic layer is washed twice with 50 ml of water, dried over sodium sulfate, the solvent is removed and the residue crystallized from hexane. Thus 3.6 g of the desired compound are obtained, yield 85%. Mp.: 61°–62° C.

PMR (CDCl$_4$): 1.42 (6H, s); 2.56 (2H, s); 6.0 (2H, s); 6.32 (1H, s); 7.14 (1H, s).

EXAMPLE 9

Preparation of
6,7-ethylenedioxy-2,2-dimethyl-4-chromanone

To a stirred mixture of 100 ml of methyl-ethyl-ketone and 2.6 ml (30 millimoles) of 1,2-dibromo ethane heated to 60° C. 4.2 g (20 millimoles) of 6,7-dihydroxy-2,2-dimethyl-4-chromanone and a suspension of 8.3 g (60 millimoles) of potassium carbonate and 0.5 g of potassium iodide in 100 ml of methyl-ethyl ketone are added dropwise within 3 hours. The reaction mixture is heated to boiling for 5 hours. The inorganic salt is filtered off, washed twice with 20 ml of acetone each and the solvent is removed. The residue is crystallized from 70% ethanol. Thus 3.75 g of the desired compound are obtained, yield 80%. Mp.: 118°–119° C.

PMR (CDCl$_3$): 1.36 (6H, s); 2.58 (2H, s); 4.2 (4H, m); 6.36 (1H, s); 7.3 (1H, s).

EXAMPLE 10

Preparation of 6,7-(1,3-propylenedioxy)-2,2-dimethyl-4-chromenone

In 50 ml of N,N-dimethyl-formamide 6 g (3 ml, 30 millimoles) of 1,3-dibromo-propane are dissolved. The solution is heated to 120° C. and at this temperature a suspension of 4.2 g of 6,7-dihydroxy-2,2-dimethyl-4-chromanone, 8.3 g (60 millimoles) of potassium carbonate, 0.5 g of potassium iodide and 50 ml of N,N-dimethyl formamide is added within 3 hours dropwise. The reaction mixture is heated at 120° C. for a further 2 hours and worked up according to Example 8. Thus 3.7 g of the desired compound are obtained in the form of a yellow oil. Yield 75%.

PMR (CDCl$_3$): 1.36 (6H, s); 2.1 (2H, m); 2.58 (2H, s); 4.2 (4H, m); 6.4 (1H, s); 7.36 (1H, s).

EXAMPLE 11

Preparation of 6,7-bis-(trifluoroethoxy)-2,2-dimethyl-4-chromanone

In 100 ml of N,N-dimethyl-formamide 4.2 g (20 millimoles) of 6,7-dihydroxy-2,2-dimethyl-4-chromanone are dissolved under nitrogen whereupon 8.3 g (60 millimoles) of potassium carbonate and 11.5 g (45 millimoles) of trifluoroethoxy tosylate are added. The reaction mixture is stirred at 120° C. for 10 hours, poured onto 200 ml of crushed ice, 100 ml of saturated sodium hydrogen carbonate solution are added and the mixture is extracted three times with 50 ml of carbon tetrachloride each. The organic phase is washed twice with 100 ml of water each, dried over anhydrous sodium sulfate and the solvent is removed. The residue is crystallized from ethanol. Thus 4.8 g of the desired compound are obtained, yield 65%. Mp.: 92°–93° C.

PMR (CDCl$_3$): 1.48 (6H, s); 2.7 (2H, s); 4.35 (4H, m); 6.5 (1H, s); 7.48 (1H, s):

| Analyse: | calculated % | Found % |
| --- | --- | --- |
| C | 48.44 | 48.39; 48.25 |
| H | 3.81 | 3.79; 3.72 |
| F | 30.58 | 30.62; 30.55. |

EXAMPLE 12

Preparation of 7-methoxymethoxy-2,2-dimethyl-4-chromanone

A mixture of 20 ml of 10% sodium hydroxide solution, 50 ml of dichloro methane, 0.5 g (2 millimoles) of triethyl benzyl ammonium chloride and 0.9 g (10 millimoles) of 7-hydroxy-2,2-dimethyl-4-chromanone is intensively stirred at 20° C. for 30 minutes. To the mixture 3.1 g (2 ml, 25 millimoles) of bromomethyl-methyl-ether are added. The reaction mixture is stirred for a further 30 minutes, the organic phase is separated, washed twice with 50 ml. of water each, dried and the solvent is removed. The residue is crystallized from 70% ethanol. Thus 2.1 g of the desired compound are obtained, yield 90%. Mp.: 77°–79° C.

PMR (CDCl$_3$): 1.38 (6H, s); 2.6 (2H, s); 3.4 (3H, s); 5.1 (2H, s); 6.5 (2H, m); 7.7 (1H, d, J=8 Hz).

EXAMPLE 13

Preparation of 7-ethoxymethoxy-2,2-dimethyl-4-chromanone

A mixture of 40 ml of an 5% sodium hydroxide solution, 60 ml of dichloro methane, 0.5 g (2 millimoles) of triethyl benzyl ammonium chloride and 1.9 g (10 millimoles) of 7-hydroxy-2,2-dimethyl-4-chromanone is intensively stirred at room temperature for 20 minutes, whereupon 2.3 g (2,2 ml, 25 millimoles) of chloromethyl-ethyl-ether are added and the reaction mixture is stirred for an hour. The reaction mixture is worked up according to Example 12. Thus 2.1 g of the desired compound are obtained in the form of a light yellow oil, yield 85%.

PMR (CDCl$_3$): 1.16 (3H, t, J=7 Hz); 1.4 (6H, s); 2.6 (2H, s); 3.66 (2H, q, J=2 Hz); 5.14 (2H, s); 6.5 (2H, m); 7.7 (1H, d, J=8 Hz).

EXAMPLE 14

Preparation of 7-(methylmercapto-methoxy)-2,2-dimethyl-4-chromanone

A mixture of 20 ml of a 10% sodium hydroxide solution, 40 ml of dichloromethane, 0.5 g (2 millimoles) of tetrabutyl-ammonium-hydrogensulfate and 10 millimoles of 7-hydroxy-2,2-dimethyl-4-chromanone is intensively stirred for 30 minutes. To the mixture 2.4 g (2,1 ml, 25 millimoles) of chloromethyl-thiomethyl-ether are added, the reaction mixture is stirred for 20 minutes at room temperature and worked up according to Example 12. Thus 2.0 g of the desired compound are obtained in the form of an orange oil, yield 79%.

PMR (CDCl$_3$): 1.36 (6H, s); 2.18 (3H, s); 2.6 (2H, s); 5.1 (2H, s); 6.36 (1H, d, J=2 Hz); 6.5 (1H, dd, J=2 Hz, respectively J=8 Hz); 7.7 (1H, d, J=8 Hz).

EXAMPLE 15

Preparation of 7-(2-hydroxy-n-propoxy)-2,2-dimethyl-4-chromanone

To a mixture of 40 ml of methanol, 5 ml of water 1.1 g (20 millimoles) of potassium hydroxide and 3.8 g (20 millimoles) of 7-hydroxy-2,2-dimethyl-4-chromanone under stirring 11.6 g (14 ml, 0.2 mole) of propene oxide are added and the reaction mixture is refluxed for 5 hours. The reaction mixture is diluted with 200 ml of water and worked up according to Example 12. Thus 4.0 g of the desired compound are obtained, yield 80%. Mp.: 111°–113° C.

PMR (acetone-d$_6$): 1.12 (3H, d, J=4 Hz); 1.36 (6H, s); 2.6 (2H, s); 3.9 (2H, d, J=5 Hz); 4.2 (2H, m+s); 6.34 (1H, d, J=2 Hz); 6.5 (1H, dd, J=2 Hz, respectively J=8 Hz); 7.7 (1H, d, J=8 Hz).

EXAMPLE 16

Preparation of 7-morpholinyl-ethoxy-2,2-dimethyl-4-chromanone

In 100 ml of methyl-ethyl-ketone 3.8 g (20 millimoles) of 7-hydroxy-2,2-dimethyl-4-chromanone are dissolved, whereupon 8.3 g (60 millimoles) of potassium carbonate, 0.5 g potassium iodide and thereafter 4.6 g (25 millimoles) of morpholinyl-ethyl-chloride hydrochloride are added and the reaction mixture is heated to boiling for 10 hours. The reaction having been completed the reaction mixture is cooled, the inorganic salt filtered off, washed twice with 20 ml of acetone each and the solvent is removed. The residue is treated with 100 ml of water. Thus 5.2 g of the desired compound are obtained in the form of white crystals, yield 85.3%. Mp.: 61°-63° C.

PMR (CCl4): 1.36 (6H, s); 2.5 (6H, m); 2.7 (2H, t, J=5 Hz); 3.54 (4H, m); 4.0 (2H, t, J=5 Hz); 6.2 (1H, d, J=2 Hz); 6.35 (1H, dd, J=2 Hz, respectively J=8 Hz); 7.6 (1H, d, J=8 Hz).

Preparation of compounds of the Formula II

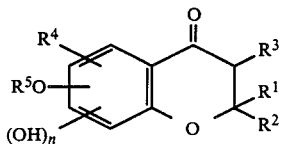

EXAMPLE 17

Preparation of 6-hydroxy-7-methoxy-2,2-dimethyl-4-chromanone

In 100 ml of acetone 4.2 g (20 millimoles) of 6,7-dihydroxy-2,2-dimethyl-4-chromanone are dissolved and to the solution thus obtained 4.1 g (30 millimoles) of potassium carbonate and 4.5 g (2 ml, 30 millimole) of methyl iodide are added under stirring. The reaction mixture is refluxed for 4 hours. The inorganic salt is filtered off, washed twice with 20 ml of acetone each and the solvent is removed. The residue is suspended in 100 ml of chloroform and extracted twice with 50 ml of a 4% sodium hydroxide solution each. The aqueous-alkaline phase is separated, cooled to 5° C. and acidified with 37% hydrochloric acid under constant stirring. The precipitated product is filtered off, washed twice with 20 ml of water each and dried to constant weight. The product is purified by recrystallization from anhydrous ethanol. Thus 4.0 g of the desired compound are obtained, yield 90%. Mp.: 134°-136° C.

IR (CCl4): $\nu$CO: 1690 cm$^{-1}$; $\nu$OH: 3570 cm$^{-1}$

PMR (CDCl3): 1.4 (6H, s); 2.62 (2H, s); 3.88 (3H, s); 6.42 (2H, s+s); 7.36 (1H, s).

EXAMPLE 18

Preparation of 6-hydroxy-7-ethoxy-2,2-dimethyl-4-chromanone

In 100 ml of methyl-ethyl-ketone 4.2 g (20 millimoles) of 6,7-dihydroxy-2,2-dimethyl-4-chromanone are dissolved. To the solution 4.1 g (30 millimoles) of potassium carbonate and 4.7 g (2.4 ml, 30 millimoles) of ethyl iodide are added and the reaction mixture is heated to boiling for 3 hours. The reaction mixture is worked up according to Example 17. Thus 4.0 g of the title compound are obtained, yield 85%. Mp.: 129°-130° C.

IR: (CCl4): $\nu$CO: 1690 cm$^{-1}$; $\nu$OH: 3570 cm$^{-1}$

PMR (CDCl3): 1.5 (9H, m); 2.64 (2H, s); 4.18 (2H, q, J=8 Hz); 6.41 (2H, s+s); 7.4 (1H, s).

EXAMPLE 19

Preparation of 6-hydroxy-7-isopropoxy-2,2-dimethyl-4-chromanone

In 80 ml of N,N-dimethyl formamide 4.2 g (20 millimoles) of 6,7-dihydroxy-2,2-dimethyl-4-chromanone are dissolved, whereupon 4.1 g (30 millimoles) of potassium carbonate and 4.2 g (2.5 ml, 25 millimoles) of isopropyl iodide are added. The reaction mixture is heated at 130° C. for 6 hours, poured into 200 ml of water and extracted with 100 ml of carbon tetrachloride. To the aqueous layer 50 ml of an 5% sodium hydroxide solution are added and the mixture is cooled below 5° C. The mixture is acidified with concentrated hydrochloric acid, the precipitated crystalline substance is filtered off and crystallized from methanol. Thus 4.5 g of the desired compound are obtained, yield 90%, mp.: 138°-139° C.

IR: (CCl4) $\nu$CO: 1690 cm$^{-1}$; $\nu$OH: 3565 cm$^{-1}$

PMR (CDCl3): 1.48 (12H, m); 2.66 (2H, s); 4.83 (1H, m); 6.0 (1H, s); 6.54 (1H, s); 7.52 (1H, s).

EXAMPLE 20

Preparation of 6-hydroxy-7-sec. butoxy-2,2-dimethyl-4-chromanone

In 100 ml of methyl-ethyl-ketone 4.2 g (20 millimoles) of 6,7-dihydroxy-2,2-dimethyl-4-chromanone are dissolved and to the solution thus obtained 4.1 g (30 millimoles) of potassium carbonate, 0.5 g of potassium iodide and 3.3 g (2.6 millimoles, 24 millimoles) of sec. butyl bromide are added under stirring. The reaction mixture is heated to boiling for 12 hours. The reaction mixture is worked up according to Example 17. Thus 4.5 g of the desired compound are obtained, yield 86%, mp.: 114°-116° C.

IR (CCl4): $\nu$CO: 1690 cm$^{-1}$; $\nu$OH: 3560 cm$^{-1}$

PMR (CDCl3): 0.97 (3H, t, J=6 Hz); 1.32 (3H, d, J=6 Hz); 1.43 (6H, s); 1.8 (2H, m); 2.63 (2H, s); 4.4 (1H, m); 6.13 (1H, s); 6.4 (1H, s); 7.36 (1H, s).

EXAMPLE 21

Preparation of 5-hydroxy-7-propargyloxy-2,2-dimethyl-4-chromanone

In 60 ml of methyl-ethyl-ketone 4.2 g of 5,7-dihydroxy-2,2-dimethyl-4-chromanone are dissolved, whereupon 3.0 g (22 millimoles) of potassium carbonate, 0.2 g of potassium iodide, and 3.0 g (2.3 ml, 25 millimoles) of propargyl bromide are added and the reaction mixture is refluxed for 4 hours. The inorganic salt is filtered off, the residue is taken up in 100 ml of carbon tetrachloride and extracted twice with 25 ml of a 5% sodium hydroxide solution each. The aqueous-alkaline layer is cooled to 0° C. The precipitated sodium phenolate salt is filtered off, washed twice with 20 ml of acetone each, and suspended in 25% hydrochloric acid (50 ml). The mixture is stirred at 5° C. for an hour. The precipitated white product is filtered off, washed twice with 20 ml of water each and dried to constant weight. The crude product thus obtained can be directly subjected to further reactions. Thus 3.7 g of the desired compound are obtained, yield 75%, Mp.: 122°-124° C.

PMR (CDCl3): 1.44 (6H, s); 2.56 (1H, m); 2.64 (2H, s); 4.64 (2H, d, J=2 Hz); 6.0 (2H, m); 12.3 (1H, s).

EXAMPLE 22

Preparation of 5-hydroxy-7-isobutoxy-2,2-dimethyl-4-chromanone

In 50 ml of diethylene glycol dimethylether (DIGLIM) 4.2 g (20 millimoles) of 5,7-dihydroxy-2,2-dimethyl-4-chromanone are dissolved, whereupon 3.0 g (22 millimoles) of potassium carbonate and 0.2 g of potassium iodide and thereafter 3.3 g (2.6 ml, 24 millimoles) of isobutyl bromide are added. The reaction mixture is heated at 100° C. for 10 hours and worked up according to Example 19. Thus 4.1 g of the desired compound are obtained, yield 79%. Mp.: 77°-79° C.

PMR (CDCl$_3$): 0.96 (6H, d, J=6 Hz); 1.4 (6H, s); 2.0 (1H, m); 2.6 (2H, s); 3.66 (2H, d, J=6 Hz); 5.9 (2H, m); 12.2 (1H, s).

EXAMPLE 23

Preparation of 7-isopropoxy-8-hydroxy-2,2-dimethyl-4-chromanone

In 50 ml of N,N-dimethyl formamide 4.2 g (20 millimoles) of 7,8-dihydroxy-2,2-dimethyl-4-chromanone are dissolved, whereupon 5 ml of diethylene glycol dimethylether, 3.0 g (22 millimoles) of potassium carbonate and 4.2 g (2.5 ml, 25 millimoles) of isopropyl iodide are added. The reaction mixture is heated at 140° C. for 4 hours and worked up according to Example 19. Thus 4.5 g of the desired compound are obtained, yield 90%, mp.: 114°–116° C.

PMR (CDCl$_3$): 1.36 (6H, d, J=6 Hz); 1.46 (6H, s); 2.66 (2H, s); 4.6 (1H, m); 6.0 (1H, s); 6.5 (1H, d, J=8 Hz); 7.34 (1H, d, J=8 Hz).

EXAMPLE 24

Preparation of 7-sec. butoxy-8-hydroxy-2,2-dimethyl-4-chromanone

In 80 ml of dimethyl sulfoxide 4.2 g (20 millimoles) of 7,8-dihydroxy-2,2-dimethyl-4-chromanone are dissolved, whereupon 10 ml of diethylene glycol dimethylether, 4.1 g (30 millimoles) of potassium carbonate, 0.5 g of potassium iodide and 3.3 g (2.6 ml, 24 millimoles) of sec. butyl bromide are added. The reaction mixture is heated at 100° C. for 10 hours, poured onto 200 ml of crushed ice and extracted with 100 ml of carbon tetrachloride. To the aqueous phase 20 ml of 10% sodium hydroxide solution are added, the mixture is cooled to 0° C., acidified with concentrated hydrochloric acid and stirred at 0° C. for 2 hours. The product is filtered, washed twice with 20 ml of water, dried and crystallised from 90% ethanol. Thus 4.4 g of the desired compound are obtained, yield 83%, mp.: 108°–110° C.

PMR (CDCl$_3$): 0.96 (3H, t, J=8 Hz); 1.3 (3H, d, J=5 Hz); 1.44 (6H, s); 1.7 (2H, m); 2.66 (2H, s); 4.3 (1H, m); 5.9 (1H, s); 6.5 (1H, d, J=8 Hz); 7.3 (1H, d, J=8 Hz).

Preparation of "mixed" chromanones of the general Formula III

EXAMPLE 25

Preparation of 6-ethoxy-7-methoxy-2,2-dimethyl-4-chromanone

In 100 ml of methyl-ethyl-ketone 4.45 g (20 millimoles) of 6-hydroxy-7-methoxy-2,2-dimethyl-4-chromanone are dissolved, whereupon 4.1 g (30 millimoles) of potassium carbonate and 4.7 g (2.4 ml, 30 millimoles) of ethyl iodide are added and the reaction mixture is refluxed for 5 hours. The precipitated inorganic salt is filtered off, washed twice with 20 ml of acetone each and the solvent is removed. The residue is crystallized from 90% ethanol. Thus 4.75 g of the desired compound are obtained, yield 95%. Mp.: 86°–87° C.

PMR (CDCl$_3$): 1.44 (9H, s+t, J=6 Hz); 2.68 (2H, s); 3.92 (3H, s); 4.14 (2H, q, J=6 Hz); 6.44 (1H, s); 7.32 (1H, s).

EXAMPLE 26

Preparation of 6-methoxy-7-ethoxy-2,2-dimethyl-4-chromanone

In 100 ml of acetone 4.7 g (20 millimoles) of 6-hydroxy-7-ethoxy-2,2-dimethyl-4-chromanone are dissolved, whereupon 4.1 g (30 millimoles) of potassium carbonate and 4.5 g (2 ml, 30 millimoles) of methyl iodide are added. The reaction mixture is refluxed for 4 hours, the inorganic salt is filtered off, washed twice with 20 ml of acetone and the half of the solvent is removed. The residue is cooled to 0° C., the precipitated product is filtered off and dried to constant weight. Thus 4.6 g of the desired compound are obtained, yield 92%. Mp.: 120°–122° C.

PMR (CDCl$_3$): 1.5 (9H, m); 2.64 (2H, s); 3.86 (3H, s); 4.16 (2H, q, J=8 Hz); 6.4 (1H, s); 7.32 (1H, s).

EXAMPLE 27

Preparation of 6-methoxy-7-sec. butoxy-2,2-dimethyl-4-chromanone

In 40 ml of a 5% sodium hydroxide solution 5.2 g (20 millimoles) of 6-hydroxy-7-sec. butoxy-2,2-dimethyl-4-chromanone are dissolved whereupon 80 ml of dichloro methane and 0.5 g of triethyl benzyl ammonium chloride are added and the mixture is intensively stirred at room temperature for 30 minutes. After the addition of 4.25 g (1.9 ml, 30 millimoles) of methyl iodide the reaction mixture is stirred for further 2 hours. The organic phase is separated, washed twice with 50 ml of water each, dried over sodium sulfate and the solvent is removed. The residue is crystallized from 90% ethanol. Thus 5.34 g of the desired compound are obtained, yield 96%. Mp.: 92.5°–93° C.

PMR (CDCl$_3$): 0.96 (3H, t, J=6 Hz); 1.34 (3H, d, J=4 Hz); 1.4 (6H, s); 1.7 (2H, m); 2.6 (2H, s); 3.8 (3H, s); 4.3 (1H, m); 6.36 (1H, s); 7.22 (1H, s).

EXAMPLE 28

Preparation of 5-methoxy-7-sec. butoxy-2,2-dimethyl-4-chromanone

In 100 ml of acetonitrile 5.6 g (20 millimoles) of the sodium salt of 5-hydroxy-7-sec. butoxy-2,2-dimethyl-4-chromanone are dissolved and stirred in the presence of 0.5 g (2 millimoles) of 18-Crown-6 for 30 minutes. Thereafter 4.25 g (1.9 ml, 30 millimoles) of methyl iodide are added and the reaction mixture is stirred for a further 3 hours. The inorganic salt is filtered off, the solvent removed and the residue suspended in carbon tetrachloride, extracted twice with 30 ml of water each, the organic phase is dried over sodium sulfate and evaporated. Thus 5.1 g of the desired compound are obtained in the form of a light yellow oil, yield 92%.

PMR (CDCl$_3$): 0.96 (3H, t, J=7 Hz); 1.3 (3H, d, J=8 Hz); 1.44 (6H, s); 1.7 (2H, m); 2.6 (2H, s); 3.85 (3H, s); 4.3 (1H, m); 6.0 (2H, m):

EXAMPLE 29

Preparation of 7-isobutoxy-8-methoxy-2,2-dimethyl-4-chromanone

In 50 ml of a 10% sodium hydroxide solution under nitrogen 5.2 g (20 millimoles) of 7-isobutoxy-8-hydroxy-2,2-dimethyl-4-chromanone are dissolved, whereupon 2.6 g (2 ml, 21 millimoles) of dimethyl sulfate are added and the reaction mixture is intensively stirred for 3 hours at 50° C. The mixture is diluted with 100 ml of icecold water, extracted three times with 50 ml of chloroform each, the organic phase is washed twice with 40 ml of water dried over sodium sulfate and the solvent is evaporated. Thus 5.2 g of the desired compound are obtained in the form of yellow oil, yield 93%.

PMR (CDCl$_3$): 0.96 (6H, dd, J=8 Hz); 1.4 (6H, s); 2.1 (1H, m); 2.6 (2H, s); 3.8 (3H, s); 3.88 (2H, m); 6.5 (1H, d, J=8 Hz); 7.56 (1H, d, J=8 Hz):

Preparation of 2H-chromenes of the Formula V

EXAMPLE 30

Preparation of 7-methoxy-2,2-dimethyl-2H-chromene (P1)

A mixture of 2.1 g (10 millimoles) of 7-methoxy-2,2-dimethyl-4-chromanone, 50 ml of tetrahydrofuran, 20 ml of water, 2.66 g (15 millimoles) of palladium chloride and 4.2 g (0,11 mole) of sodium tetrahydro borate is stirred at 0° C. for 20 minutes and thereafter at 5° C. for a further 4 hours. The reaction mixture is filtered, the filtrate extracted twice with 50 ml of chloroform each. The solvent is distilled off, the residue taken up in 50 ml of toluene and distilled in the presence of anhydrous potassium hydrogen sulfate for 20 minutes. The reaction having been completed the organic phase is washed twice with 20 ml of water each and the solvent is removed. The crude product is purified by column chromatography. Thus 1.75 g of the desired compound are obtained in the form of a colorless oil, yield 85%.

PMR (CDCl$_3$): 1.36 (6H, s); 3.64 (3H, s); 5.36 (1H, d, J=10 Hz); 6.16 (1H, d, J=10 Hz); 6.3 (2H, m); 6.76 (1H, d, J=8 Hz).

EXAMPLE 31

Preparation of 6,7-dimethoxy-2,2-dimethyl-2H-chromene (P2)

In a mixture of 75 ml of tetrahydrofurane and 25 ml of ethanol 4.7 g (20 millimoles) of 6,7-dimethoxy-2,2-dimethyl-4-chromanone are dissolved, whereupon 1.5 g (40 millimoles) of sodium tetrahydro borate are added in small portions. The reaction mixture is heated to boiling for an hour, cooled to 15° C., whereupon 50 ml of 4N hydrochloric acid are added and the mixture is stirred at a temperature not exceeding 20° C. for 3 30 minutes. The two-phase layer is separated, the aqueous phase is extracted twice with 40 ml of petrol-ether (30°–40° C.) each, the organic phases are collected, washed twice with 25 ml of 5% sodium hydroxide solution and twice with 40 ml water each, dried over sodium sulfate and evaporated. The residue is crystallized from 80% methanol. Thus 4.0 g of the desired compound are obtained, yield 92%. Mp.: 46°–47° C.

PMR (CCl$_4$): 1.34 (6H, s); 3.69 (3H, s); 3.72 (3H, s); 5.38 (1H, d, J=10 Hz); 6.18 (1H, d, J=10 Hz); 6.36 (1H, s); 6.48 (1H, s).

EXAMPLE 32

Preparation of 6-methoxy-7-ethoxy-2,2-dimethyl-2H-chromene (P3)

In 80 ml of anhydrous tetrahydrofurane 5.0 g (20 millimoles) of 6-methoxy-7-methoxy-2,2-dimethyl-4-chromanone are dissolved whereupon 1.5 g of lithium aluminum hydride are added in small portions under stirring and the reaction mixture is heated to boiling for an hour. The reaction mixture is worked up according to Example 31. The product is purified by column chromatography. Thus 4.1 g of the desired compound are obtained in the form of a colorless oil, yield 88%.

PMR (CDCl$_3$): 1.45 (9H, m); 3.8 (3H, s); 4.1 (2H, q, J=8 Hz); 5.48 (1H, d, J=10 Hz); 6.28 (1H, d, J=10 Hz); 6.46 (1H, s); 6.6 (1H, s).

EXAMPLE 33

Preparation of 5-methoxy-7-sec. butoxy-2,2-dimethyl-2H-chromene

In a mixture of 60 ml of tetrahydrofuran and 40 ml of methanol 5.6 g (20 millimoles) of 5-methoxy-7-sec. butoxy-2,2-dimethyl-4-chromanone are dissolved, whereupon 1.5 g (40 millimoles) of sodium tetrahydroborate are added in small portions and the reaction mixture is heated to boiling for 2 hours. The reaction mixture is worked up according to Example 31. The product is purified by column chromatography. Thus 4.4 g of the desired compound are obtained in the form of a light yellow oil, yield 85%.

PMR (CDCl$_3$): 0.92 (3H, t, J=8 Hz); 1.24 (3H, d, J=8 Hz); 1.36 (6H, s); 1.6 (2H, m); 3.7 (3H, s); 4.2 (1H, m); 5.3 (1H, d, J=10 Hz); 5.92 (2H, m); 6.5 (1H, d, J=10 Hz).

EXAMPLE 34

Preparation of 7-sec. butoxy-8-methoxy-2,2-dimethyl-2H-chromene

In 100 ml of tetrahydrofuran 5.6 g (20 millimoles) of 7-sec. butoxy-8-methoxy-2,2-dimethyl-4-chromanone are dissolved. To the solution 1.5 g of lithium aluminium hydride are added in small portions under stirring and the reaction mixture is heated to boiling for 2 hours. The reaction mixture is worked up according to Example 31. The product is purified by column chromatography. Thus 4.2 g of the desired compound in the form of a colorless oil, yield 80%.

PMR (CDCl$_3$): 0.96 (3H, t, J=8 Hz); 1.24 (3H, d, J=8 Hz); 1.4 (6H, s); 1.7 (2H, m); 3.76 (3H, s); 4.2 (1H, m); 5.4 (1H, d, J=10 Hz), 6.16 (1H, d, J=10 Hz); 6.32 (1H, d, J=8 Hz); 6.56 (1H, d, J=8 Hz).

Remarks: The conditions used at column chromatography are as follows:
adsorbent: Kieselgel-60
eluent: a 9:1 mixture of hexane and ether.

EXAMPLES 35–188

The new compounds enumerated in Table II and the known compounds disclosed in Table III are prepared by the processes according to the previous Examples [Compounds III/1 and III/2 serve as reference compound]

TABLE II

Compounds of the Formula V $$\text{(V')}$$

| No. | $R_1$ | $R_2$ | $R_3$ | $R_4$ | $R_5$ | $R_6$ | $R_7$ | $R_8$ | |
|---|---|---|---|---|---|---|---|---|---|
| 1 | Me | Me | H | H | H | H | nPrO | H | TT—35 |
| 2 | Me | Me | H | H | H | H | iPrO | H | TT—36 |
| 3 | Me | Me | H | H | H | H | iBuO | H | TT—39 |
| 4 | Me | Me | H | H | H | H | c-pentyl-O | H | TT—40 |
| 5 | Me | Me | H | H | H | H | $CH_3-O-CH_2-O$ | H | TT—77 |
| 6 | Me | Me | H | H | H | H | $CH_3-S-CH_2-O$ | H | |
| 7 | Me | Me | H | H | H | H | $EtO-CH_2-O$ | H | TT—78 |
| 8 | Me | Me | H | H | H | H | crotyl-O | H | |
| 9 | Me | Me | H | H | H | H | prenyl-O | H | |
| 10 | Me | Me | H | H | H | H | benzyl-O | H | TT—41 |
| 11 | Me | Me | H | H | Me | H | EtO | H | TT—52 |
| 12 | Me | Me | H | H | Me | H | nPrO | H | TT—53 |
| 13 | Me | Me | H | H | Me | H | iPrO | H | TT—54 |
| 14 | Me | Me | H | H | Me | H | nBuO | H | |
| 15 | Me | Me | H | H | Me | H | sec.BuO | H | TT—55 |
| 16 | Me | Me | H | H | Me | H | iBuO | H | TT—56 |
| 17 | Me | Me | H | H | Me | H | c-pentyl-O | H | TT—57 |
| 18 | Me | Me | H | H | Me | H | benzyl-O | H | |
| 19 | Me | Me | H | H | Me | H | $CH_3-O-CH_2-O$ | H | |
| 20 | Me | Me | H | H | Me | H | $CH_3-S-CH_2-O$ | H | |
| 21 | Me | Me | H | H | Me | H | $Et-O-CH_2-O$ | H | |
| 22 | Me | Me | H | H | Me | H | $CH\equiv C-CH_2-O$ | H | TT—58 |
| 23 | Me | Me | H | H | H | H | EtO | Me | |
| 24 | Me | Me | H | H | H | H | iPrO | Me | |
| 25 | Me | Me | H | H | H | H | sec.BuO | Me | |
| 26 | Me | Me | H | H | H | H | iBuO | Me | |
| 27 | Me | Me | H | H | H | H | $CH_3-O-CH_2-O$ | Me | |
| 28 | Me | Me | H | H | H | H | $CH_3-S-CH_2-O$ | Me | |
| 29 | Me | Me | H | H | H | H | $Et-O-CH_2-O$ | Me | |
| 30 | Me | Me | H | H | H | H | $CH\equiv C-CH_2-O$ | Me | |
| 31 | Me | Me | H | H | H | iBuO | iBuO | H | TT—19 |
| 32 | Me | Me | H | H | H | benzyl-O | benzyl-O | H | TT—20 |
| 33 | Me | Me | H | H | H | $CF_3CH_2-O$ | $OF_3CH_2-O$ | H | TT—15 |
| 34 | Me | Me | H | H | H | allyl-O | allyl-O | H | TT—08 |
| 35 | Me | Me | H | H | H | crotyl-O | crotyl-O | H | TT—12 |
| 36 | Me | Me | H | H | H | prenyl-O | prenyl-O | H | TT—13 |
| 37 | Me | Me | H | H | H | $CH\equiv C-CH_2-O$ | $CH\equiv C-CH_2-O$ | H | |
| 38 | Me | Me | Cl | Cl | H | EtO | EtO | H | TT—27 |
| 39 | Me | Me | Cl | Cl | H | iPrO | iPrO | H | TT—28 |
| 40 | Me | Me | Cl | Cl | H | MeO | EtO | H | TT—30 |
| 41 | Me | Me | Cl | Cl | H | MeO | iPrO | H | TT—31 |
| 42 | Me | Me | H | H | H | MeO | sec.BuO | H | TT—23 |
| 43 | Me | Me | H | H | H | MeO | iBuO | H | TT—24 |
| 44 | Me | Me | H | H | H | MeO | c-pentyl-O | H | TT—43 |
| 45 | Me | Me | H | H | H | MeO | benzyl-O | H | TT—25 |
| 46 | Me | Me | H | H | H | —O—$(CH_3)_2$C—O | | H | TT—87 |
| 47 | Me | Me | H | H | H | MeO | krotyl-O | H | |
| 48 | Me | Me | H | H | H | MeO | prenyl-O | H | TT—14 |
| 49 | Me | Me | H | H | MeO | H | EtO | H | TT—59 |
| 50 | Me | Me | H | H | MeO | H | nPrO | H | TT—60 |
| 51 | Me | Me | H | H | MeO | H | iPrO | H | TT—61 |
| 52 | Me | Me | H | H | MeO | H | sec.BuO | H | TT—62 |
| 53 | Me | Me | H | H | MeO | H | iBuO | H | TT—63 |
| 54 | Me | Me | H | H | H | H | EtO | MeO | TT—64 |
| 55 | Me | Me | H | H | H | H | nPrO | MeO | TT—65 |
| 56 | Me | Me | H | H | H | H | iPrO | MeO | TT—66 |
| 57 | Me | Me | H | H | H | H | sec.BuO | MeO | TT—67 |
| 58 | Me | Me | H | H | H | H | iBuO | MeO | TT—68 |
| 59 | Me | H | Me | H | H | MeO | MeO | H | TT—72 |
| 60 | Me | H | Me | H | MeO | H | MeO | H | |
| 61 | Me | H | Me | H | H | H | MeO | MeO | |
| 62 | Me | H | Me | H | Me | H | MeO | H | |
| 63 | Me | H | Me | H | H | H | MeO | Me | |
| 64 | Me | H | Me | H | H | H | MeO | H | |
| 65 | Me | H | Me | H | H | MeO | EtO | H | |
| 66 | Me | H | Me | H | H | MeO | nPrO | H | |
| 67 | Me | H | Me | H | H | MeO | iPrO | H | |
| 68 | Me | H | Me | H | H | MeO | sec.BuO | H | |
| 69 | Me | H | Me | H | H | MeO | iBuO | H | |
| 70 | Me | H | Me | H | H | MeO | $CH\equiv C-CH_2-O$ | H | |

TABLE II-continued

Compounds of the Formula V $$\text{(V')}$$

| No. | R₁ | R₂ | R₃ | R₄ | R₅ | R₆ | R₇ | R₈ |
|-----|----|----|----|----|----|----|----|-----|
| 71 | Me | Me | H | Me | H | MeO | EtOOCCH₂—O | H |
| 72 | Me | Me | H | Me | H | MeO | benzyl-O | H |
| 73 | Me | Me | H | Me | H | benzyl-O | benzyl-O | H |

TABLE III

Compounds of the general Formula V

| No. | R₁ | R₂ | R₃ | R₄ | R₅ | R₆ | R₇ | R₈ |
|-----|----|----|----|----|----|----|----|-----|
| 1 | H | H | H | H | H | H | H | H |
| 2 | Me | Me | H | H | H | H | H | H |
| 3 | Me | Me | H | H | MeO | H | H | H |
| 4 | Me | Me | H | H | H | MeO | H | H |
| 5 | Me | Me | H | H | H | H | MeO | H |
| 6 | Me | Me | H | H | H | H | H | MeO |
| 7 | Me | Me | H | H | HOC | H | H | H |
| 8 | Me | Me | H | H | H₃COC | H | H | H |
| 9 | Me | Me | H | H | H | EtO | H | H |
| 10 | Me | Me | H | H | H | nPrO | H | H |
| 11 | Me | Me | H | H | H | nBuO | H | H |
| 12 | Me | Me | H | H | H | CH₃CO | H | H |
| 13 | Me | Me | H | H | H | CH₃OOC—C(CH₃)= | H | H |
| 14 | Me | Me | H | H | H | H | EtO | H |
| 15 | Me | Me | H | H | H | H | nBuO | H |
| 16 | Me | Me | H | H | H | H | sec.BuOn | H |
| 17 | Me | Me | H | H | H | H | tBuO | H |
| 18 | Me | Me | H | H | H | H | nPentO | H |
| 19 | Me | Me | H | H | H | H | EtO—(CH₂)₂O | H |
| 20 | Me | Me | H | H | H | H | CH≡C—CH₂—O | H |
| 21 | Me | Me | H | H | H | H | HOC— | H |
| 22 | Me | Me | H | H | H | H | H₃COC— | H |
| 23 | Me | Me | H | H | H | H | CH₃C≡C—CH₂—O | H |
| 24 | Me | Me | H | H | H | H | CH₂=CH—CH₂—O | H |
| 25 | Me | Me | H | H | H | H | CF₃CH₂O | H |
| 26 | Me | Me | H | H | H | Br | MeO | H |
| 27 | Me | Me | H | H | H | Br | EtO | H |
| 28 | H | H | H | H | H | MeO | MeO | H |
| 29 | H | Me | H | H | H | MeO | MeO | H |
| 30 | Me | Me | H | H | H | MeO | MeO | H |
| 31 | Me | Et | H | H | H | MeO | MeO | H |
| 32 | Et | Et | H | H | H | MeO | MeO | H |
| 33 | H | phenyl | H | H | H | MeO | MeO | H |
| 34 | Me | 3,4-methylenedioxyphenyl | H | H | H | MeO | MeO | H |
| 35 | Me | CF₃ | H | H | H | MeO | MeO | H |
| 36 | Me | Me | H | H | H | EtO | EtO | H |
| 37 | Me | Me | H | H | H | nPrO | nPrO | H |
| 38 | Me | Me | H | H | H | iPrO | iPrO | H |
| 39 | Me | Me | H | H | H | nBuO | nBuO | H |
| 40 | Me | Me | H | H | H | sec.BuO | sec.BuO | H |
| 41 | Me | Me | H | H | H | tBuO | tBuO | H |
| 42 | Me | Me | H | H | H | nPentO | nPentO | H |
| 43 | Me | Me | H | H | H | MeO | EtO | H |
| 44 | Me | Me | H | H | H | EtO | MeO | H |
| 45 | Me | Me | H | H | H | MeO | iPrO | H |

TABLE III-continued

| | | | | | Compounds of the general Formula V | | |
|---|---|---|---|---|---|---|---|
| No. | $R_1$ | $R_2$ | $R_3$ | $R_4$ | $R_5$ | $R_6$ | $R_7$ | $R_8$ |
| 46 | Me | Me | H | H | H | iPrO | MeO | H |
| 47 | Me | Me | H | H | H | MeO | nPrO | H |
| 48 | Me | Me | H | H | H | MeO | nBuO | H |
| 49 | Me | Me | H | H | H | MeO | nHexO | H |
| 50 | Me | Me | H | H | H | O—CH$_2$—O | | H |
| 51 | Me | Me | H | H | H | O—(CH$_2$)—O | | H |
| 52 | Me | Me | H | H | H | CH≡C—CH$_2$—O | MeO | H |
| 53 | Me | Me | H | H | H | CH$_2$=CH—CH$_2$—O | MeO | H |
| 54 | Me | Me | H | H | H | MeO | CH≡C—CH$_2$—O | H |
| 55 | Me | Me | H | H | H | MeO | CH$_2$=CH—CH$_2$—O | H |
| 56 | Me | Me | H | H | H | MeO | CF$_3$CH$_2$—O | H |
| 57 | Me | Me | H | H | H | CF$_3$CH$_2$—O | MeO | H |
| 58 | Me | Me | H | H | H | MeO | MeO | H |
| 59 | Me | Me | H | H | MeO | MeO | H | H |
| 60 | Me | Me | H | H | MeO | H | MeO | H |
| 61 | Me | Me | H | H | H | MeO | H | MeO |
| 62 | Me | Me | H | H | H | H | MeO | Me |
| 63 | Me | Me | H | H | MeO | MeO | MeO | H |
| 64 | Me | Me | H | H | MeO | H | MeO | CH$_3$CO |
| 65 | Me | Me | H | H | MeO | CH$_3$COO | MeO | H |
| 66 | Me | Me | H | H | MeO | H | Me | CH$_3$COO |
| 67 | H | H | Me | H | H | MeO | MeO | H |
| 68 | Me | Me | H | Me | H | MeO | MeO | H |
| 69 | Me | Me | H | H | Me | H | MeO | H |
| 70 | Me | Me | Cl | Cl | H | H | H | H |
| 71 | Me | Me | Cl | Cl | H | MeO | H | H |
| 72 | Me | Me | Cl | Cl | H | H | MeO | H |
| 73 | Me | Me | Cl | Cl | H | MeO | MeO | H |
| 74 | Me | Me | Cl | Cl | H | —OCH$_2$—O— | | H |
| 75 | Me | Me | F | H | H | MeO | MeO | H |
| 76 | Me | Me | F | H | H | —O—CH$_2$—O— | | H |
| 77 | Me | Me | F | H | MeO | H | H | H |
| 78 | Me | Me | F | H | H | H | MeO | H |
| 79 | Me | Me | F | H | Me | H | Me | H |
| 80 | Me* | Me | F | H | H | CH CO | H | H |
| 81 | Me | Me | F | H | OH | CH CO | H | H |

EXAMPLE 189

Preparation of 50 EC formulation of the active ingredient

| Component | Amount |
|---|---|
| Active ingredient of the Formula V | 500 g$^x$ |
| "Arylan" C.A. | 64,2 g |
| "Lubrol" N 15 | 40,0 g |
| Aromasol | filled up to 1000.0 ml |

$^x$ = related to 100% of active ingredient

Remark: the above composition is diluted with water and the spray thus obtained is used for testing the activity of the compounds of the general Formula V.

The chromene derivatives enumerated in Tables II and III can be prepared in an analogous manner to Examples 1–34.

EXAMPLE 190

Determined of insecticidal and nematocidal effect of compounds of the Formula V

Test Pests

Insects:
 Cotton bug (*Dysdercus fasciatus*)
 cabbage butterfly (*Pieris brassicae*)
 mustard beetle
 domestic fly (*Musca domestica*)
 pea plant-louse (*Acirtosypon pisi*)
 Colorado beetle
Nematodes:
 *Caenorhabditis elegans*
 tomato root gall nematode (*Meloidogyne incognita*).

The details of the tests are discussed below.

(1) Cotton bug test

A dilution series is prepared from the test compound with acetone and 0.2 μl of each dilution is topically applied onto the back part of larvae of the II. stage of growth with the aid of a Hamiltion syringe. The active ingredient is absorbed through the cuticula. The animals are kept in a large glass and fed with cotton grains and water. After adult shedding the surviving insects are observed for eventual adultoid symptoms, the egg-reproduction and the development of the ovules is evaluated too.

(2) Cabbage butterfly

From the 50 EC of the test compound a diluted series is prepared with water and the host seedlings (cabbage) are sprayed with this composition until the spray runs down. The spray is allowed to dry whereupon 20 young larvae of the II. stage are placed on each treated plant and the seedlings are kept under so-called "long-day" illumination (18 hours of illumination and 6 hours of darkness). The nibbled plants are replaced by similarly sprayed plants if necessary. The killing rate of the insects, the growth rate of the larvae and the morphological deformations of the surviving nymphs and adults are registered.

(3) Mustard beetle

Two weeks' old mustard seedlings are sprayed with a solution of 0.1 g of the test compound, 0.5 ml of dimethyl sulfoxide, and 10 μl of 50 EC composition in 10 ml of water. After the spray is dried, 20 mustard larvae of the II. stage are placed on each plant. The sprayed plants are changed every second day. The evaluation is based on the number of the imagos hotching from the nymphs.

(4) Domestic fly

The fly larvae are grown on a nutrient medium of the following composition: 2 ml of milk; 2 ml of water; 2 g of wheat bran; 0.1 ml of saturated alcoholic nipagin solution.

The nutrient medium is filled into cylindrical glass vials (30×100 mm) and 25 fly larvae are raised in each vial. The test compound is dissolved in milk; the end concentration (related to milk) amounts to 0.1% which corresponds to 0.05% (related to the total nutrient medium). The solution of the active ingredient is admixed with the nutrient medium whereupon 25 ml of domestric fly larvae of the I. stage are placed into each vial and the vials are closed with a hard cotton-wool stopper. The nymphs emerging from the larvae are collected in each vial, counted and kept in a Petri dish (diameter 25 mm) until flies hatch from the nymphs. The hatched flies are counted.

(5) Caenorhabditis elegans 0.5 ml of the acetonous solution of the test compound is applied onto a NGM agar plate free from bacteria in a Petri dish. After the acetone has dried 25–30 young adults are placed on the plate. After 24 hours the surviving and killed insects are counted.

(6) Root gall nematode

The test is carried out on II. stage infective larvae, which are collected from the root of tomato plant, placed on a filter and incubated in sterile water at 25° C. The hatched larvae are collected every 24 hours and immediately placed onto the treated nutrient medium. As nutrient medium NGM agar plate free from bacteria is used. 0.5 ml of the acetoneous solution of the test compound is applied onto the surface of the plate in a Petri-dish. After the acetone has evaporated 5 μl of the larva suspension is applied onto each plate. After 72 hours the surviving and killed insects are counted.

The test results are summarized in the following Tables.

(Remark: in the cotton bug test 50 insects are used).

In each Table the results obtained with the control group are disclosed as well.

The following test compounds are used in the biological experiments.

TABLE IV

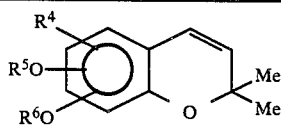

| No. | R⁵O— | R⁶O— | R⁴ |
|---|---|---|---|
| 1 | 6 MeO | 7 MeO | H |
| 2 | 6 EtO | 7 EtO | H |
| 3 | 6 MeO | 7 EtO | H |
| 4 | 6 O—CH₂—O 7 | | H |
| 5 | 6 allylO | 7 allylO | H |
| 6 | 6 iPrO | 7 iPrO | H |
| 7 | 6 MeO | 7 allylO | H |
| 8 | 6 MeO | 7 iPrO | H |
| 9 | 6 crotylO | 7 crotylO | H |
| 10 | 6 prenylO | 7 prenylO | H |
| 11 | 6 MeO | 7 prenylO | H |
| 12 | 6 CF₃CH₂O | 7 CF₃CH₂O | H |
| 13 | 6 nPrO | 7 nPrO | H |
| 14 | 6 nBuO | 7 nBuO | H |
| 15 | 6 sec.BuO | 7 sec.BuO | H |
| 16 | 6 iBuO | 7 iBuO | H |
| 17 | 6 benzylO | 7 benzylO | H |
| 18 | 6 MeO | 7 nPrO | H |

TABLE IV-continued

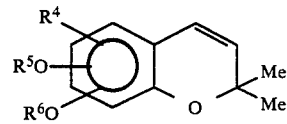

| No. | R⁵O— | R⁶O— | R⁴ |
|---|---|---|---|
| 19 | 6 MeO | 7 nBuO | H |
| 20 | 6 MeO | 7 sec.BuO | H |
| 21 | 6 MeO | 7 iBuO | H |
| 22 | 6 MeO | 7 benzylO | H |
| 23 | H | 7 MeO | H |
| 24 | H | 7 EtO | H |
| 25 | H | 7 nPrO | H |
| 26 | H | 7 iPrO | H |
| 27 | H | 7 nBuO | H |
| 28 | H | 7 sec.BuO | H |
| 29 | H | 7 iBuO | H |
| 30 | H | 7 c-pentylO | H |
| 31 | H | 7 benzylO | H |
| 32 | H | 7 MeO | 5 Me |
| 33 | 6 MeO | 7 c-pentylO | H |
| 34 | 6 EtO | 7 MeO | H |
| 35 | 7 MeO | 8 MeO | H |
| 36 | 5 MeO | 7 MeO | H |
| 37 | H | 7 propargylO | H |
| 38 | H | 7 EtO | 5 Me |
| 39 | H | 7 nPrO | 5 Me |
| 40 | H | 7 iPrO | 5 Me |
| 41 | H | 7 sec.BuO | 5 Me |
| 42 | H | 7 iBuO | 5 Me |
| 43 | H | 7 c-pentylO | 5 Me |
| 44 | H | 7 propargylO | 5 Me |
| 45 | 5 MeO | 7 EtO | H |
| 46 | 5 MeO | 7 nPrO | H |
| 47 | 5 MeO | 7 iPrO | H |
| 48 | 5 MeO | 7 sec.BuO | H |
| 49 | 5 MeO | 7 iBuO | H |
| 50 | 7 EtO | 8 MeO | H |
| 51 | 7 nPrO | 8 MeO | H |
| 52 | 7 iPrO | 8 MeO | H |
| 53 | 7 sec.BuO | 8 MeO | H |
| 54 | 7 iBuO | 8 MeO | H |
| 55 | H | H | H |
| 56 | 6 O—(CH₃)₂C—O 7 | | H |

TABLE V/1

Effect of the test compounds on cotton bug

| Test compound | LD₅₀ (μg/insect) | AJH effect (μg/insect) | Sterilizing effect (μg/insect) |
|---|---|---|---|
| 1 (P2) | 0.6 | 1 | 10 |
| 3 | 0.5 | 10 | 10 |
| 8 | 0.45 | 1 | 0.2 |
| 10 | 0.6 | — | — |
| 20 | 0.4 | 0.1 | — |
| 21 | 0.4 | — | — |
| control⁺ | — | — | — |

⁺ = when the insects are treated with acetone, the survival rate is 90-95%.

TABLE V/2

Effect of the test compound on cabbage butterfly

| Test compound | Killing rate of larvae % | Survival nymph % | Survival adult % |
|---|---|---|---|
| 23 (P1) | 41 | 59 | 50 |
| 25 | 52 | 48 | 39 |
| 38 | 81 | 19 | 19 |
| 41 | 11 | 19 | 14 |
| 42 | 100 | — | — |
| 43 | 100 | — | — |
| 44 | 83 | 17 | 17 |
| 46 | 88 | 12 | 12 |
| 47 | 87 | 13 | 9 |
| 48 | 100 | — | — |

TABLE V/2-continued

Effect of the test compound on cabbage butterfly

| Test compound | Killing rate of larvae % | Survival nymph % | Survival adult % |
| --- | --- | --- | --- |
| 49 | 100 | — | — |
| 50 | 76 | 24 | 24 |
| 51 | 100 | — | — |
| 52 | 64 | 36 | 32 |
| 53 | 100 | — | — |
| 54 | 93 | 7 | 7 |
| control[x] | 12 | 88 | 88 |

+ = EC composition containing no active ingredient.

In the 50 EC compositions the concentration of compounds 23 and 25 amounts to 0.01% and that of the other compounds to 0.1%.

TABLE V/3

Effect of the test compounds on mustard beetle

| Test compound | Concentration | Survival, adults (%) |
| --- | --- | --- |
| 42 | 1% | 27 |
| 51 | 1% | 45 |
| control | 0% | 100 |

TABLE V/4

Effect of the test compounds on domestic fly

| Test compound | Survival nymph (%) | Survival adult (%) |
| --- | --- | --- |
| 23 (P1) | 100 | 33.3 |
| 28 | 115 | 25.6 |
| 29 | 100 | 28.2 |
| 34 | 85 | 12.8 |
| 35 | 12 | 0 |
| 38 | 40 | 14.8 |
| 40 | 50.9 | 27.6 |
| 41 | 25.4 | 12.5 |
| 42 | 45.4 | 25.5 |
| 43 | 52.7 | 31.8 |
| 44 | 50.9 | 10.6 |
| 46 | 9.1 | 6.4 |
| 49 | 0 | 0 |
| 50 | 5.4 | 4.2 |
| 51 | 12 | 0 |
| 52 | 12 | 0 |
| Control | 100 | 100 |

TABLE V/5

Effect of the test compounds on adult *Caenorhabditis elegans* nematodes

| Test Compound | Concentration/ ug/ml | Lethality % | Size of descendant population | Remarks |
| --- | --- | --- | --- | --- |
| 1 (P2) | 200 | 100 | no descendants | |
| | 400 | 100 | no descendants | |
| 3 (P3) | 200 | 70 | some descendants | |
| | 400 | 90 | no descendants | |
| 4 | 100 | 100 | no descendants | |
| | 200 | 100 | no descendants | |
| | 400 | 100 | no descendants | |
| 5 | 200 | 40 | some descendants | |
| | 400 | 90 | no descendants | |
| 7 | 200 | 90 | no descendants | |
| | 400 | 90 | no descendants | |
| 8 | 200 | 70 | reduced | |

TABLE V/5-continued

Effect of the test compounds on adult *Caenorhabditis elegans* nematodes

| Test Compound | Concentration/ ug/ml | Lethality % | Size of descendant population | Remarks |
| --- | --- | --- | --- | --- |
| 14 | 400 | 80 | no descendants | |
| | 200 | 30 | reduced | |
| | 400 | 80 | reduced | |
| 23 (P1) | 200 | 44 | reduced | |
| | 400 | 98 | no descendants | |
| 34 | 200 | 15 | reduced | paralysation |
| | 400 | 23 | some descendants | paralysation |
| 35 | 200 | 67 | reduced | paralysation |
| | 400 | 100 | no descendants | paralysation |
| 37 | 200 | 100 | no descendants | paralysation |
| | 400 | 100 | no descendants | paralysation |
| 44 | 200 | 20 | some descendants | paralysation |
| | 400 | 30 | no descendants | paralysation |
| 50 | 200 | 40 | reduced | |
| | 400 | 100 | no descendants | |
| 52 | 200 | 60 | reduced | |
| | 400 | 73 | reduced | |
| 53 | 200 | 25 | reduced | |
| | 400 | 85 | reduced | |
| Control 10% acetone | — | 0 | normal | |

TABLE V/6

Effect of test compounds on tomato root gall nematodes (mortality %)

| Test compound | Dose μg/ml | 1. % (in parentheses the number of individuals is disclosed) | 2. % | Average % | Nematocidal effect |
| --- | --- | --- | --- | --- | --- |
| 1 (P2) | 400 | 98(65) | 95(55) | 97 | strong |
| | 200 | 76(42) | 76(42) | 76 | strong |
| 2 | 400 | 83(40) | 90(20) | 87 | strong |
| | 200 | 74(38) | 69(32) | 72 | strong |
| 3 (P3) | 400 | 100(13) | 95(40) | 97 | strong |
| | 200 | 24(62) | 20(50) | 22 | — |
| 4 | 400 | 96(65) | 92(60) | 94 | strong |
| | 200 | 84(45) | 69(70) | 77 | strong |
| 5 | 400 | 45(31) | 43(56) | 44 | medial |
| | 200 | 18(11) | 29(21) | 23 | — |
| acetone 10% Control | | 3(56) | 0(28) | 1.5 | inactive |
| NGM | | 0(41) | 6(49) | 2 | inactive |
| | | 0(40) | 3(48) | | |

What we claim is:

1. A compound selected from the group consisting of: 7-n-propoxy-8-methoxy-2,2-dimethyl-2H-chromene; 7-sec.-butoxy-8-methoxy-2,2-dimethyl-2H-chromene; and 7-isobutoxy-8-methoxy-2,2-dimethyl-2H-chromene.

2. 7-n-propoxy-8-methoxy-2,2-dimethyl-2H-chromene as defined in claim 1.

3. An insecticidal composition effective against *musca domestica* or the Colorado beetle which comprises as active ingredient an insecticidally effective amount of the compound defined in claim 1, in admixture with an insecticidally suitable solid or liquid carrier, diluent, filler, conditioning, wetting or dispersing agent.

4. A method of killing *musca domestica* or a Colorado beetle which comprises the step of contacting said *musca domestica* or said Colorado beetle with an insecticidally effective amount of the composition defined in claim 3.

* * * * *